US00PP19978P3

(12) United States Plant Patent
Elphick

(10) Patent No.: US PP19,978 P3
(45) Date of Patent: May 12, 2009

(54) MANGO PLANT NAMED 'TFE 02'

(50) Latin Name: *Mangifera indica*
Varietal Denomination: TFE 02

(76) Inventor: Richard Elphick, P.O. Box 48 Malelane, 1320, Mpumalanga (ZA)

( * ) Notice: Subject to any disclaimer, the term of this patent is extended or adjusted under 35 U.S.C. 154(b) by 122 days.

(21) Appl. No.: 11/171,808

(22) Filed: Jun. 30, 2005

(65) Prior Publication Data

US 2005/0241027 P1 Oct. 27, 2005

(51) Int. Cl.
*A01H 5/00* (2006.01)

(52) U.S. Cl. ..... Plt./159

(58) Field of Classification Search ..... Plt./263.1, Plt./381, 159
See application file for complete search history.

(56) References Cited

PUBLICATIONS

GTITM UPOVROM Citation For 'TFE 02'as Per ZA PBR 0404; Dec. 2, 2003.*

* cited by examiner

*Primary Examiner*—Kent L Bell
(74) *Attorney, Agent, or Firm*—C. A. Whealy

(57) ABSTRACT

A new and distinct cultivar of Mango plant named 'TFE 02', characterized by its upright and outwardly spreading tree form; vigorous growth habit; freely fruiting habit; time of fruit maturity, mid to late season; and red-colored fruit.

2 Drawing Sheets

Botanical designation: *Mangifera indica.*
Cultivar denomination: 'TFE 02'.

BACKGROUND OF THE INVENTION

The present Invention relates to a new and distinct cultivar of Mango plant, botanically known as *Mangifera indica* and hereinafter referred to by the name 'TFE 02'.

The new Mango is a product of a planned breeding program conducted by the Inventor in Malelane, Mpumalanga, Republic of South Africa. The objective of the breeding program was to develop new Mango cultivars with precocious reliable fruiting and medium-sized attractively-colored fruit.

The new Mango originated from an open-pollination in Malelane, Mpumalanga, Republic of South Africa of the *Mangifera indica* cultivar Haden, not patented, as the female, or seed, parent with an unidentified selection of *Mangifera indica.* The new Mango was discovered and selected by the Inventor as a single plant within the progeny of the open-pollination in a controlled environment in Malelane, Mpumalanga, Republic of South Africa.

Asexual reproduction of the new Mango by grafting in a controlled environment in Hoedspruit, Republic of South Africa has shown that the unique features of this new Mango are stable and reproduced true to type in successive generations.

SUMMARY OF THE INVENTION

The cultivar TFE 02 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'TFE 02'.

These characteristics in combination distinguish 'TFE 02' as anew and distinct cultivar of Mango:

1. Upright and outwardly spreading tree form.
2. Vigorous growth habit.
3. Freely fruiting habit.
4. Time of fruit maturity, mid to late season.
5. Red-colored fruit.

Plants of the new Mango can be compared to plants of the female parent, the cultivar Haden. In side-by-side comparisons conducted in Hoedspruit, Republic of South Africa, plants of the new Mango differed from plants of the cultivar Haden in the following characteristics:

1. Plants of the new Mango were more vigorous than plants of the cultivar Haden.
2. Plants of the new Mango had longer leaves than plants of the cultivar Haden.
3. Plants of the new Mango had shorter inflorescences than plants of the cultivar Haden.
4. Time of fruit maturity of plants of the new Mango was later than time of fruit maturity of plants of the cultivar Haden.
5. Plants of the new Mango and the cultivar Haden differed in fruit skin and flesh coloration.

Plants of the new Mango can be compared to plants of the Mango cultivar Keitt, not patented. In side-by-side comparisons conducted in Hoedspruit, Republic of South Africa, plants of the new Mango differed primarily from plants of the cultivar Keitt in the following characteristics:

1. Plants of the new Mango were more vigorous than plants of the cultivar Keitt.
2. Plants of the new Mango had narrower leaves than plants of the cultivar Keitt.
3. Plants of the new Mango had shorter inflorescences than plants of the cultivar Keitt.

4. Time of fruit maturity of plants of the new Mango was earlier than time of fruit maturity of plants of the cultivar Keitt.
5. Plants of the new Mango and the cultivar Keitt differed in fruit skin and flesh coloration.

BRIEF DESCRIPTION OF THE PHOTOGRAPHS

The accompanying colored photographs illustrate the overall appearance of the new Mango, showing the colors as true as it is reasonably possible to obtain in colored reproductions of this type. Colors in the photographs may differ slightly from the color values cited in the detailed botanical description which accurately describe the actual colors of the new Mango.

The photograph at the top of the sheet comprises a side perspective view of a typical tree of 'TFE 02' with developing fruit.

The photograph at the bottom of the first sheet is a close-up view of a typical fruit of 'TFE 02'.

The photograph at the top of the second sheet is a close-up view of typical leaves of 'TFE 02'.

The photograph at the bottom of the second sheet is a close-up view of a typical inflorescence of 'TFE 02'.

DETAILED BOTANICAL DESCRIPTION

The aforementioned photographs, following observations and measurements describe two to three-year old plants grown in Hoedspruit, Republic of South Africa in an outdoor nursery and under conditions typical of commercial Mango production. In the following description, color references are made to The Royal Horticultural Society Colour Chart, 2001 Edition, except where general terms of ordinary dictionary significance are used.

Botanical classification:
*Mangifera indica* cultivar TFE 02

Parentage:
*Female, or seed, parent.*—*Mangifera indica* cultivar Haden, not patented.
*Male, or pollen, parent.*—Unidentified selection of *Mangifera indica,* not patented.

Plant description:
*Plant form.*—Upright and outwardly spreading tree.
*Growth habit.*—Rapid; vigorous.
*Plant height.*—About 1.8 meters to 2.7 meters.
*Plant spread.*—About 1.2 meters to 2.2 meters.
*Trunk diameter, about* 30 *cm above the soil surface.*—About 7 cm to 11 cm.

Foliage description:
*Arrangement.*—Alternate; simple.
*Length.*—About 21.4 cm.
*Width.*—About 5.25 cm.
*Shape.*—Narrowly oblong.
*Apex.*—Attenuate.
*Base.*—Acute.
*Margin.*—Entire.
*Aspect.*—Twisting; concave.
*Texture, upper and lower surfaces.*—Smooth, glabrous.
*Fragrance.*—Crushed developing leaves will emit a terpinolene aroma.
*Petiole length.*—About 6 cm.
*Color.*—Developing foliage, upper and lower surfaces: 143A; towards the base, overlain with weak anthocyanin, N199B. Fully expanded foliage, upper and lower surfaces: 139A; venation, 144A. Petiole, upper and lower surfaces: 144A.

Inflorescence description:
*Appearance.*—Single rounded flowers arranged in terminal panicles; no flower bracts observed.
*Time of flowering.*—Plants typically flower from June to August in the Republic of South Africa.
*Inflorescence length.*—About 4.6 cm.
*Inflorescence diameter.*—About 17.5 cm.
*Quantity of flowers per inflorescence.*—About 2,125.

Flower description:
*Height.*—About 3.6 mm.
*Diameter.*—About 7.4 mm.
*Petals.*—Quantity per flower: About five in a single whorl. Length: About 3.6 mm. Diameter: About 1.7 mm. Shape: Oblong to lanceolate. Apex: Broadly acute. Base: Rounded. Margin: Entire. Texture, upper and lower surfaces: Smooth, glabrous. Color, immature and mature, upper and lower surfaces: 3D streaked with 175C.
*Sepals.*—Quantity per flower: About five in a single whorl. Length: About 2.9 mm. Diameter: About 1.3 mm. Shape: Lanceolate. Apex: Narrowly acute. Base: Rounded. Margin: Entire. Texture, upper and lower surfaces: Smooth, glabrous; pubescence at the margins. Color, immature and mature, upper and lower surfaces: 150C.

Fruit description:
*Time of fruit maturity.*—Mid to late season; usually about two to three weeks later than plants of the cultivar Kent, not patented.
*Length.*—About 10.9 cm.
*Diameter.*—About 8.8 cm.
*Weight.*—About 350 grams to 465 grams.
*Shape.*—Elliptic; neck not prominent; depth of stalk cavity, shallow; groove in left shoulder shallow; sinus proximal of stylar scar absent; bulge proximal of stylar scar strongly expressed.
*Texture, skin.*—Smooth, glabrous.
*Texture, flesh.*—Fine, not fibrous.
*Firmness, flesh.*—Firm.
*Thickness.*—Relatively medium to thick.
*Skin color, mature.*—Between 137C and 147B blushed with 181A.
*Skin color, ripe.*—163A blushed with 180A to 180B.
*Color, flesh.*—22A.
*Turpentine flavor.*—Not detected.
*Brix percentage.*—About 15.3; when fully ripened, about 19.5.
*Acidity.*—Relatively low.
*Seed shape.*—Reniform.

Pathogen/pest resistance: Plants of the new Mango have not been observed to be resistant to pathogens and pests common to Mangos.

It is claimed:

1. A new and distinct cultivar of mango plant named 'TFE 02' as illustrated and described.

* * * * *

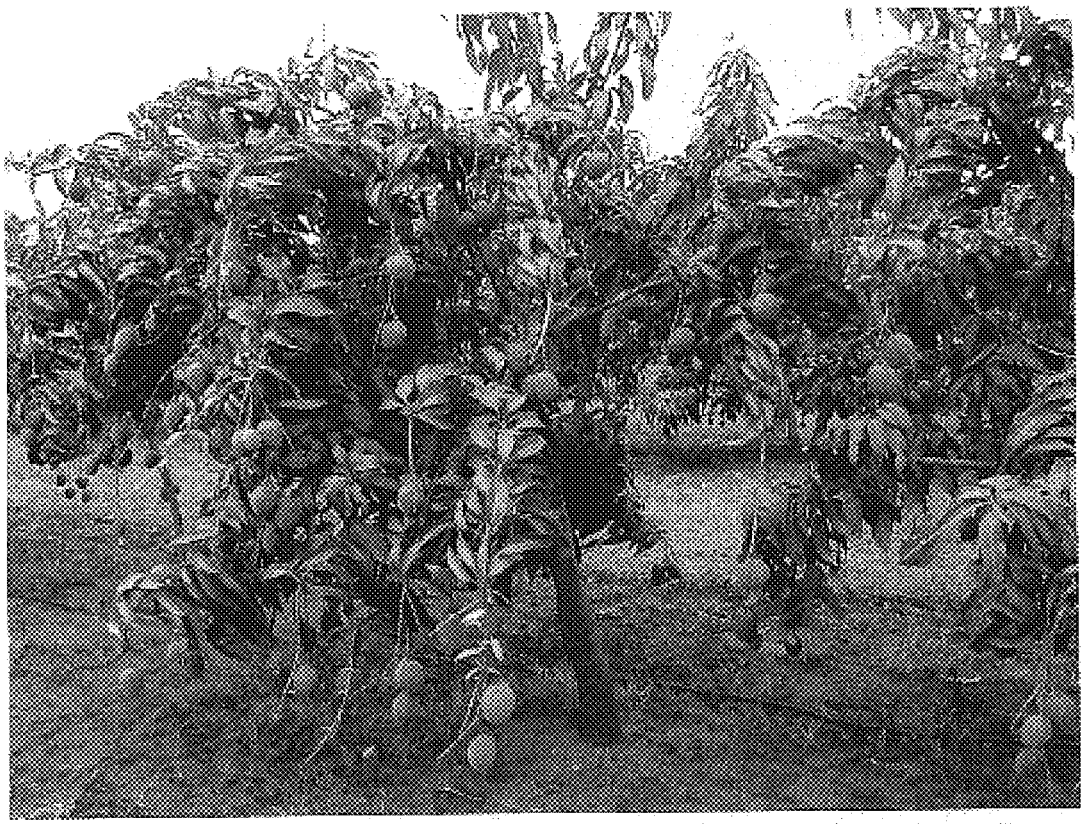
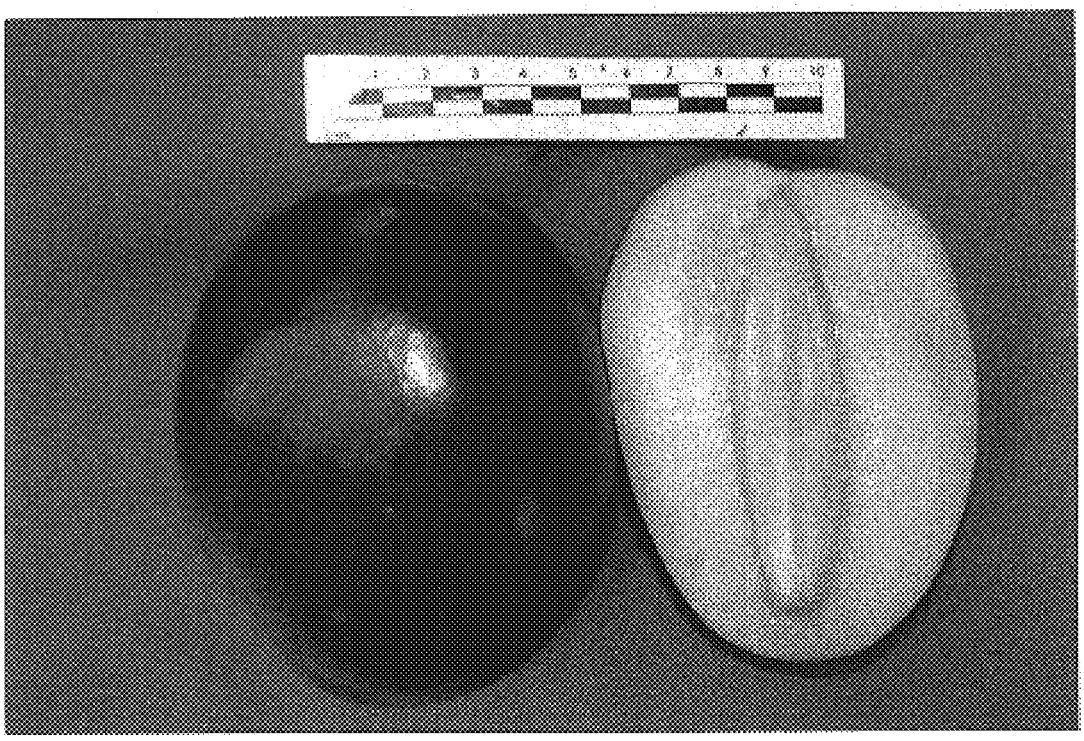

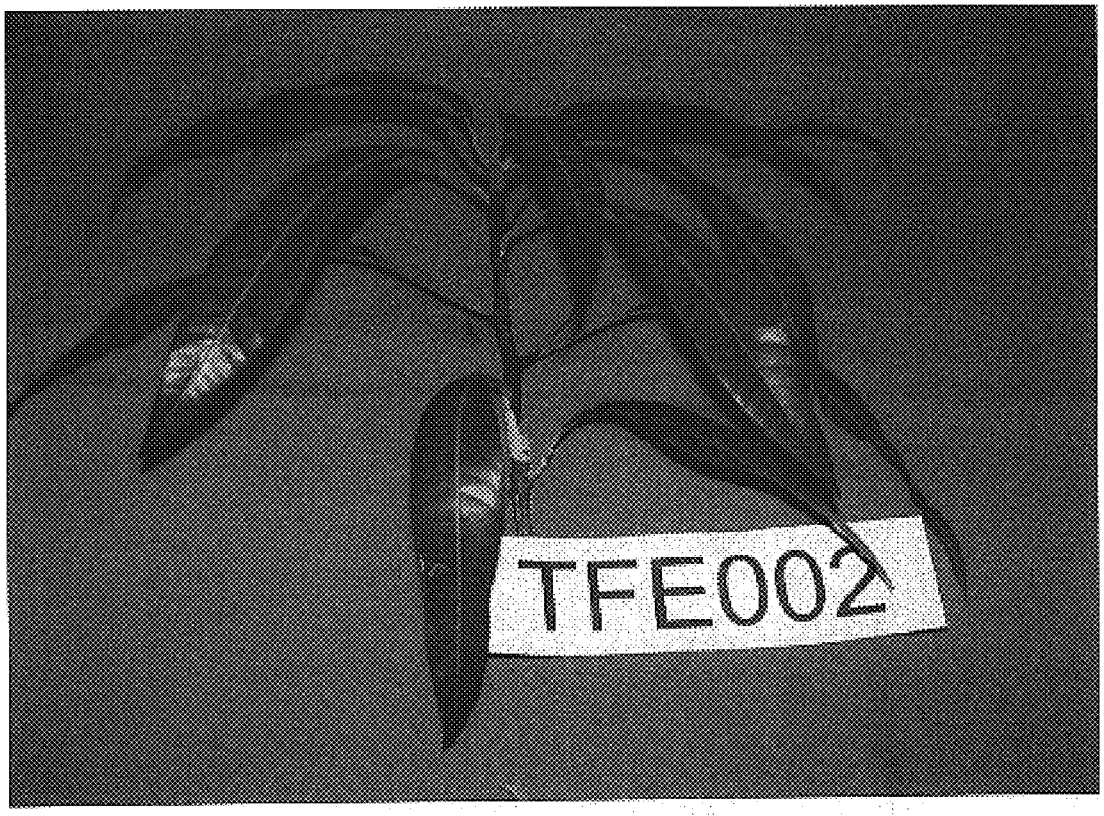
TFE002
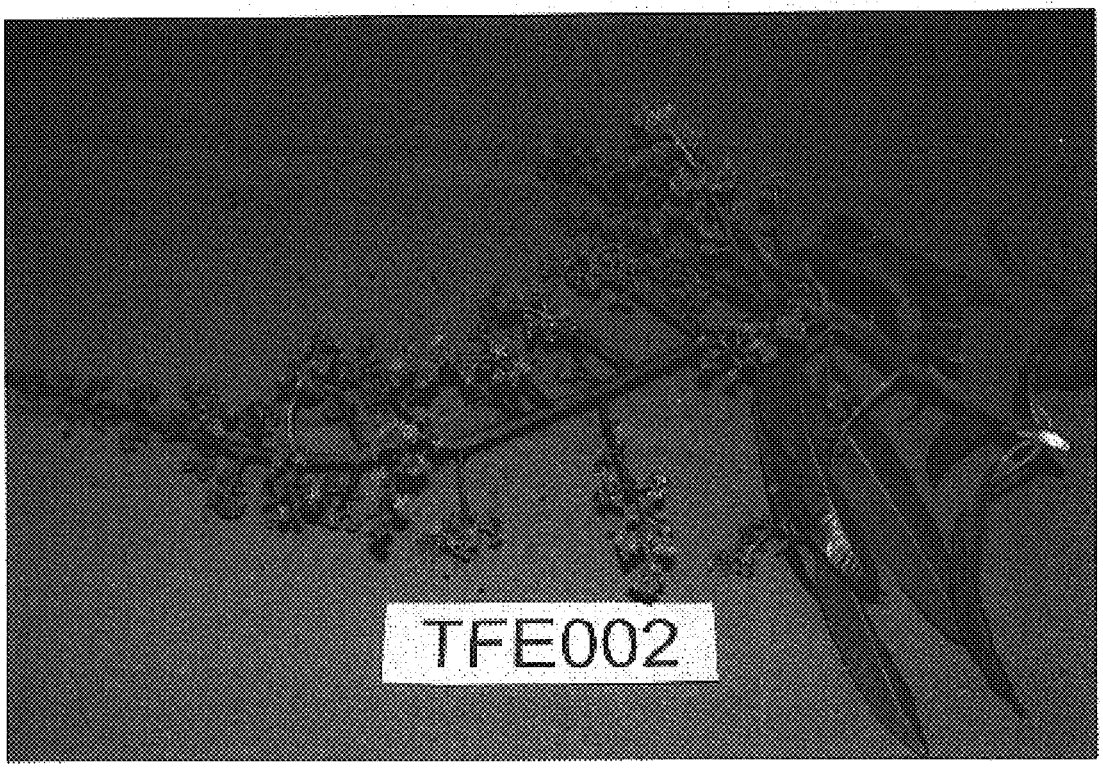
TFE002